United States Patent
Cho et al.

(10) Patent No.: US 11,730,859 B2
(45) Date of Patent: Aug. 22, 2023

(54) METHOD OF DECELLULARIZATION OF KIDNEY TISSUES, DECELLULARIZED MATERIAL BY THE METHOD AND BIOINK COMPRISING THE DECELLULARIZED MATERIAL

(71) Applicant: POSTECH Research and Business Development Foundation, Pohang-si (KR)

(72) Inventors: Dong-Woo Cho, Seoul (KR); Jae Yun Kim, Seoul (KR); Jae Yeon Lee, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 317 days.

(21) Appl. No.: 17/021,130

(22) Filed: Sep. 15, 2020

(65) Prior Publication Data

US 2021/0268150 A1    Sep. 2, 2021

(30) Foreign Application Priority Data

Mar. 2, 2020  (KR) .................. 10-2020-0026003

(51) Int. Cl.
| | |
|---|---|
| *A61L 27/36* | (2006.01) |
| *A61L 27/38* | (2006.01) |
| *A61L 27/52* | (2006.01) |
| *A61L 27/54* | (2006.01) |

(52) U.S. Cl.
CPC .......... *A61L 27/3683* (2013.01); *A61L 27/38* (2013.01); *A61L 27/52* (2013.01); *A61L 27/54* (2013.01); *A61L 2300/254* (2013.01)

(58) Field of Classification Search
None
See application file for complete search history.

(56) References Cited

U.S. PATENT DOCUMENTS

2016/0051731 A1    2/2016  Matsuda et al.

FOREIGN PATENT DOCUMENTS

KR    10-2016-0025502    3/2016

OTHER PUBLICATIONS

Destefani et al., "Advances in the knowledge about kidney decellularization and repopulation", Frontiers in Bioengineering and Biotechnology vol. 5, Article 34, pp. 1-28 (Jun. 2017).*
Andrea Porzionato et al., "Tissue-Engineered Grafts from Human Tissue-Engineered Grafts from Human Review and Future Perspectives", Iint. J. Mol. Sci. 2018, 19(12), 4117, pp. 1-79, Dec. 18, 2018. doi:10.3390/ijms19124117.
Jinah Jang et al., "Tailoring mechanical properties of decellularized extracellular matrix bioink by vitamin B2-induced photo-crosslinking", Acta Biomaterialia, vol. 33, pp. 88-95(2016). http://dx.doi.org/10.1016/j.actbio.2016.01.013.
KIPO, Office Action of KR 10-2020-0026003 dated Oct. 29, 2020.

* cited by examiner

*Primary Examiner* — Anand U Desai
(74) *Attorney, Agent, or Firm* — Lex IP Meister, PLLC

(57) ABSTRACT

The method for decellularization of kidney tissue according to the present invention, the decellularized material produced through the method, and a bioink comprising the decellularized material have the effect of maximizing the effect of kidney treatment by maximizing the content of components specialized for kidney treatment such as the collecting duct and renal tubule of the kidney.

8 Claims, 19 Drawing Sheets

SECURING
KIDNEY ORGAN

SECURING
SECTIONS

WASHING WITH
DISTILLED WATER

DECELLULARIZATION

FREEZE DRYING

Wound healing test

METHOD OF DECELLULARIZATION OF KIDNEY TISSUES, DECELLULARIZED MATERIAL BY THE METHOD AND BIOINK COMPRISING THE DECELLULARIZED MATERIAL

CROSS-REFERENCE TO RELATED APPLICATIONS

Priority to Korean patent application number 10-2020-0026003 filed on Mar. 2, 2020 the entire disclosure of which is incorporated by reference herein, is claimed.

BACKGROUND OF THE DISCLOSURE

Field of the Disclosure

The present disclosure relates to a method for decellularization of kidney tissue, a decellularized material produced through the method, and a bioink including the same, and more specifically, to a decellularized material effective for treating kidney disease.

Related Art

Chronic kidney disease (CKD) refers to the condition in which the renal function to remove waste products is deteriorated and is in a state that cannot be restored to normal. This is a symptom that occurs due to a long-term decrease in renal function, and it eventually progresses to end-stage renal disease (ESRD) requiring renal replacement therapy. Currently, treatments such as treatment of complications for the underlying causes, treatment for delaying loss of renal function, drug-based treatment, kidney replacement therapy (e.g., dialysis, transplantation, etc.), etc. are being conducted depending on the symptoms, but direct treatment for damaged kidneys has not yet been done. In addition, there is no direct therapeutic agent available for treating the damaged kidney. In the case of CKD and ESRD, the major pathologies include damage to glomerulus and fibrosis of kidney tissue, which directly affect the kidney function. Delaying the progression of this pathogenesis plays an important role in the regeneration of kidney tissue.

Currently, most studies on biomaterials derived from the extracellular matrices of decellularized kidneys are either basic studies with the aim to find an appropriate method for decellularization; or one-dimensional studies that have limitations in the production of kidney structures that reflect various cellular structures and microstructures of real kidneys, such as simply recellularization after renal tissue decellularization, etc. In connection with this prior art, Korea Patent Application Publication No. 10-2016-0025502 has been disclosed.

Such prior art is only focused on a simple decellularization process, even with respect to tissue-derived materials that are already developed. However, there are numerous types of tissues inside the organs, and the extracellular matrix components along with their functions vary in tissue by tissue. In addition, animal disease models for evaluating the efficacy of renal disease treatment is not well established. For direct regeneration and improvement of the renal function, it is necessary to develop a new type of therapeutic agent and a reliable animal disease modeling that can confirm its efficacy.

SUMMARY OF THE DISCLOSURE

An object of the present disclosure is to provide a decellularization method to overcome the limitations of conventional therapeutic agents for the treatment of renal disease, a decellularized material, and a bioink including the decellularized material.

As a method to solve the above object, according to the present invention, a method for decellularization of kidney tissue, which includes: a step of preparing kidney tissue, in which the kidney tissue obtained from a mammal to be a subject of decellularization is cut into small pieces; a step of removing cells, in which the native kidney tissue slices are converted into a decellularized material using a decellularization solution that includes a surfactant and a hypertonic solution; a step of sterilization, in which the decellularized material and a sterilization solution are stirred such that the microorganisms present in the decellularized material are killed; and a step of pH adjustment and dilution, in which an enzymatic reaction is performed such that the glycoproteins in the decellularized material are decomposed.

On the other hand, the range of acidity in pH adjustment and dilution may vary depending on the type of enzyme (more detailed, pH4.5~pH8.5, more specifically pH5-pH8), and the dilution factor may be 2 to 40 times depending on the type of enzyme and the concentration of the initial bioink.

Meanwhile, the enzyme used in the pH adjustment and dilution may be MMP-13, and in this case, the glycoproteins to be decomposed may be at least one of decorin and glycan.

Further, the pH adjustment and dilution may be performed using MMP-13 at a concentration of 2 μM to 1 M.

In addition, the pH adjustment and dilution may be performed for 3 to 5 hours.

Meanwhile, the surfactant a nonionic surfactant that can minimize damage to proteins contained in kidney tissue.

In addition, a surfactant may be Triton X-100.

Meanwhile, the method, after the step of preparing kidney tissue, the step of removing cells, and the step of sterilization, may further include a step of washing, in which the remaining solution and impurities are washed.

In addition, the step of washing may be performed by stirring the kidney tissue or decellularized material along with a washing solution.

Meanwhile, after the step of removing cells, a step of sterilization may be performed, in which a sterilization solution and the decellularized material are stirred such that the microorganisms present in the decellularized material are killed. In particular, the sterilization solution may be a solution including peracetic acid.

In addition, the sterilization solution may further include phosphate buffered saline (PBS).

Meanwhile, the method, before and after performing the step of pH adjustment and dilution, may further include a step of freeze drying that is performed at least once.

In addition, according to the present invention, a decellularized material of kidney tissue produced by performing: a step of preparing kidney tissue, in which the kidney tissue obtained from a mammal to be a subject of decellularization is cut into small pieces; a step of removing cells, in which the native kidney tissue slices are converted into a decellularized material using a decellularization solution that comprises a surfactant and a hypertonic solution; a step of sterilization, in which the decellularized material and a sterilization solution are stirred such that the microorganisms present in the decellularized material are killed; and a step of pH adjustment and dilution, in which an enzymatic reaction is performed such that the glycoproteins in the decellularized material are decomposed, may be provided.

In addition, according to the present invention, a bioink including a decellularized material of kidney tissue, wherein the bioink comprises a hydrogel configured to be 3D printed with the decellularized material, wherein the decellularized material is produced by performing: a step of preparing kidney tissue, in which the kidney tissue obtained from a mammal to be a subject of decellularization is cut into small pieces; a step of removing cells, in which the native kidney tissue slices are converted into a decellularized material using a decellularization solution that comprises a surfactant and a hypertonic solution; a step of sterilization, in which the decellularized material and a sterilization solution are stirred such that the microorganisms present in the decellularized material are killed; and a step of pH adjustment and dilution, in which an enzymatic reaction is performed such that the glycoproteins in the decellularized material are decomposed, may be provided.

Meanwhile, a hydrogel may include at least one of gelatin and collagen.

In addition, the hydrogel may be configured to be liquefied at a predetermined temperature or below.

DESCRIPTION OF EXEMPLARY EMBODIMENTS

Figure 1:
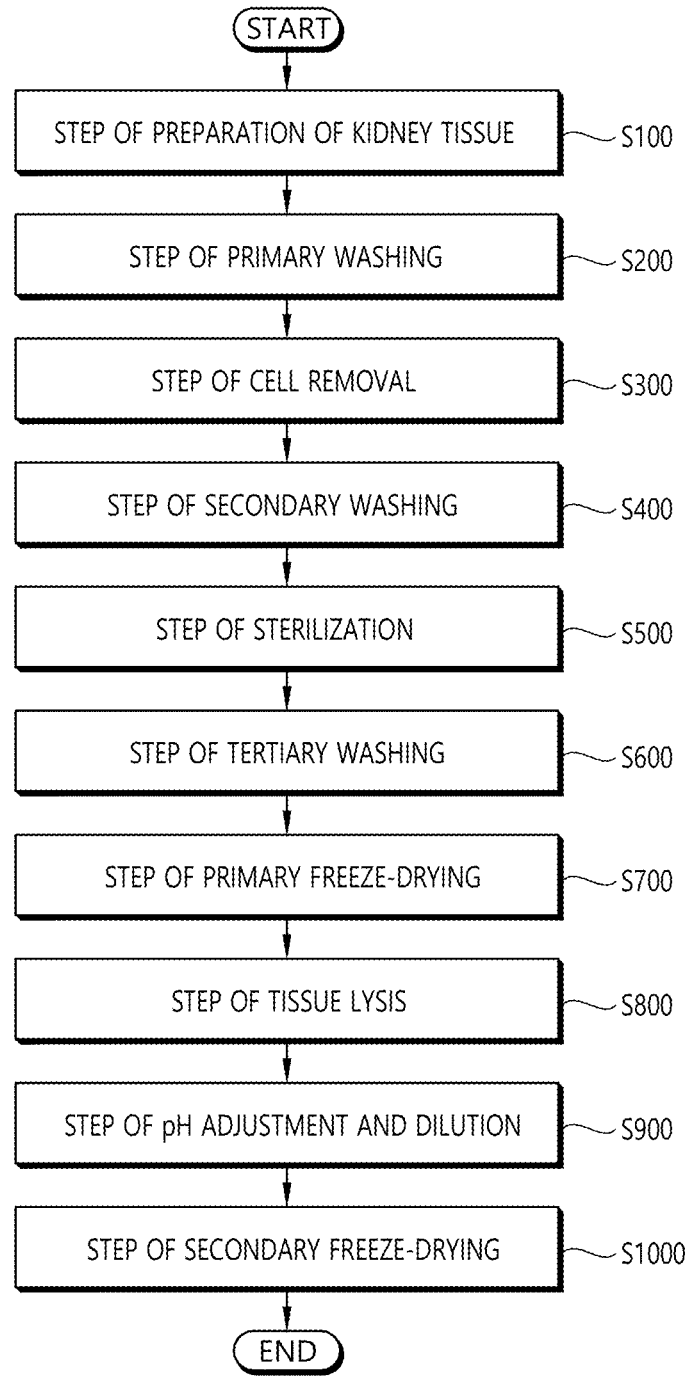
FIG. 1 is a flow chart illustrating decellularization of kidney tissue according to one embodiment.

Hereinafter, a method for decellularization of kidney tissue according to an embodiment of the present invention, a decellularized material produced through the same method, and a bioink including the decellularized material will be described in detail with reference to the accompanying drawings. In addition, in the following description of the embodiments, the names of each component may be referred to as other names in the art. However, when they have functional similarity and identity, they may be regarded as a uniform configuration even when a modified embodiment is adopted. In addition, codes added to each component are described for convenience of description. However, the illustrated contents on the drawings in which these codes are described do not limit each component to the range in the drawing. Similarly, even when an embodiment in which some modifications of the configuration on the drawing are adopted, it can be regarded as an equivalent configuration if there are functional similarity and identity. In addition, in light of the level of a person of general skill in the art, when it is recognized as a component that should be included, description thereof will be omitted.

Figure 2:
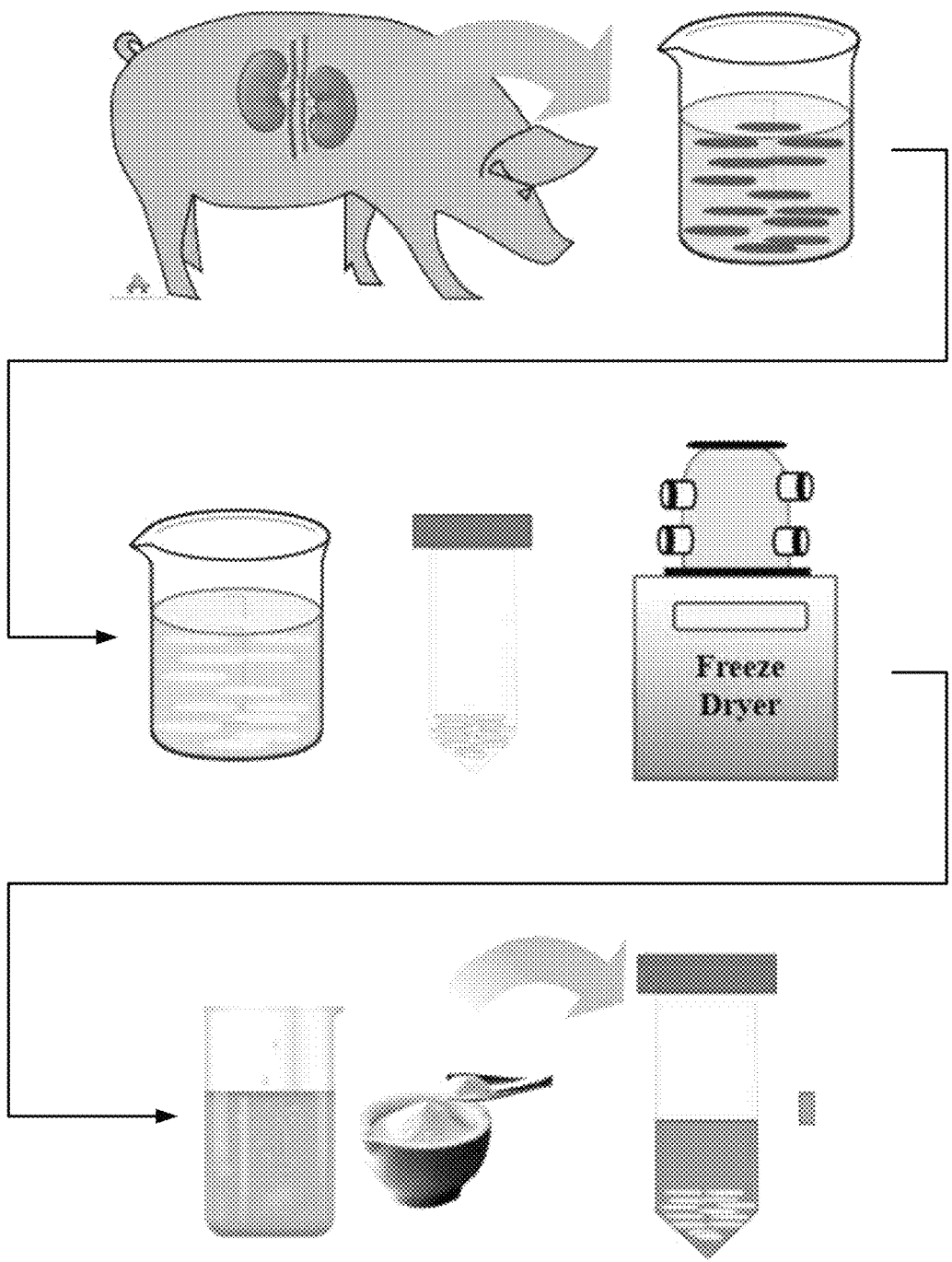
FIG. 2 is a diagram illustrating the concept of decellularization of kidney tissue according to an embodiment.
Figure 3A:
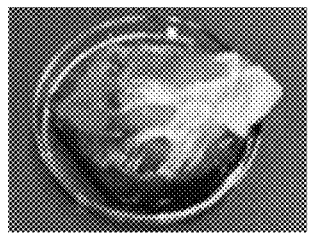
FIGS. 3A, 3B, 3C, 3D, 3E and 3F shows images illustrating a decellularized material of kidney tissue according to an embodiment.
Figure 3B:
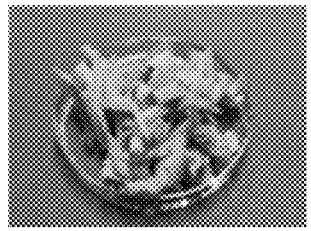
Figure 3C:
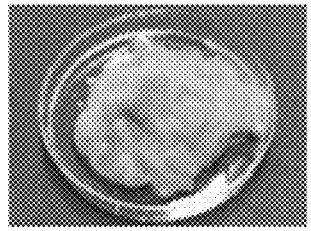
Figure 3D:
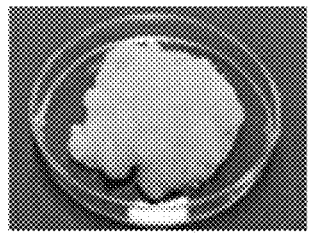
Figure 3E:
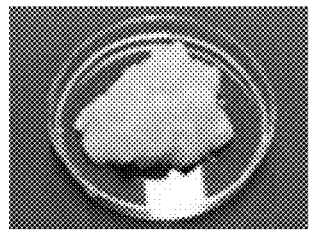
Figure 3F:

FIG. 1 is a flow chart illustrating decellularization of kidney tissue according to one embodiment; and FIG. 2 is a diagram illustrating the concept of decellularization of kidney tissue according to an embodiment. As illustrated, decellularization of kidney tissue, which is an embodiment according to the present invention, is performed by including specific steps to maximize a material specialized in kidney treatment. In particular, an example of the material specialized in kidney treatment may be laminin, which is known to be a core tissue extracellular matrix component that is effective in the regeneration of collecting ducts and tubules of the kidneys.

In this embodiment, the decellularized material prepared by the kidney tissue decellularization method can be used as a material for kidney bioink upon the achievement of standards for sterilization and remnant cellular contents. For this purpose, in the present invention, the decellularization of kidney tissue may include a decellularization process (S100 to S600) and a process for the production of bioink raw materials (S700 to S1000).

The decellularization process may be constituted to include a step of kidney tissue preparation (S100), a step of primary washing (S200), a step of cell removal (S300), a step of secondary washing (S400), a step of sterilization (S500), and a step of tertiary washing (S600).

The step of kidney tissue preparation (S100) first corresponds to a step of preparing kidney tissue obtained from a mammal. Kidney tissue is first obtained from the mammal, and is then prepared by cutting it into small pieces with an appropriate size. For example, in order to increase the yield and efficiency in a decellularization process, which will be described later, the kidney tissue may be prepared by cutting it to a thickness of 2 mm or less. Further, the kidney tissue may be prepared in small pieces by pulverization, etc.

The step of primary washing (S200) is configured to remove impurities or a remaining solution contained in the prepared kidney tissue. The step of kidney tissue preparation (S100) may be performed using a washing solution. The washing solution may be, for example, distilled water, and in this case, the step of primary washing (S200) may be performed by mixing and stirring the washing solution and distilled water together. In the step of primary washing (S200), as the tissue is washed, unnecessary materials (e.g., blood contained in the tissue, etc.) are removed from the tissue, and it can be confirmed that the color of the tissue fades when visually confirmed. The step of kidney tissue preparation (S100) may be performed, for example, in a state in which the mass of distilled water is 10 times or more compared to that of the tissue. In addition, the step of primary washing (S200) may be performed, for example, at room temperature for 15 to 30 minutes at a time, and may be performed three times by replacing the washing solution. In this case, the total time of performing the step of primary washing (S200) may be from 1 hour to 1 hour and 30 minutes. However, the above time of performing the step of primary washing (S200) is only an example and the step of primary washing (S200) may be appropriately selected and performed as a sufficient washing time.

The step of cell removal (S300) corresponds to a decellularization process of kidney tissue. The step of cell removal (S300) is performed to destroy the DNA of cells contained in the kidney tissue while minimizing damage to various proteins, glycoproteins, glycosaminoglycan (GAG), etc. contained in the cells and extracellular matrix.

The step of cell removal (S300) may be performed using a decellularization solution containing a surfactant and a hypertonic solution. The surfactant may be, for example, a nonionic surfactant, and specifically, Triton X-100 within 1% may be included therein. The hypertonic solution is used along with a surfactant to improve the efficiency of decellularization, and it may be composed at a concentration higher than normal saline. As an example of the hypertonic solution, a NaCl solution of 0.3 M to 1.0 M may be used.

The step of cell removal (S300) may be performed under the condition that the ratio of kidney tissue and a decellularization solution is 1/10 or less. That is, the step of cell removal (S300) may be performed when the mass of the kidney tissue is within 10% of the solution, and in this respect, it was experimentally confirmed that the step of cell removal (S300) could proceed efficiently when the volume of the kidney tissue is within 10% of the solution with the boundary of 10% of the solution.

The step of cell removal (S300) is performed by mixing and stirring kidney tissue and a decellularization solution together, and it may be performed by periodically replacing with a newly prepared decellularization solution so that decellularization of kidney tissue can be continuously performed. In an embodiment, the replacement cycle of the decellularization solution may be determined such that it is replaced every 3 hours. However, this is only an embodiment, and the replacement cycle may be determined at an appropriate time and frequency so that the decellularization solution can be maintained at a concentration capable of exerting a sufficient decellularization effect.

The step of cell removal (S300) may be performed at room temperature and it may be performed for a time not exceeding 75% compared to the entire decellularization process. In an embodiment, when the time required for the entire decellularization process (S100 to S600) is 40 hours, the step of cell removal (S300) may be performed for 15 to 16 hours. When the time for performing the step of cell removal (S300) is too short, it is difficult to expect sufficient decellularization of kidney tissue. In contrast, when the performance time is too long, the loss of the active ingredients such as extracellular matrix proteins and growth factors necessary for the treatment of kidney tissue may increase. Therefore, it is preferable to perform the step of cell removal (S300) at an appropriate duration. Meanwhile, with respect to the replacement of the decellularization solution above, when the step of cell removal (S300) is performed for 15 to 16 hours, the replacement of the decellularization solution may be performed 4 to 6 times.

The step of secondary washing (S400) is configured to remove the decellularization solution and impurities after the step of cell removal (S300). In this step (S400), it may be performed similarly to the step of primary washing (S200) described above, and in an embodiment, and the step (S400) may be performed using distilled water at room temperature for 15 to 30 minutes at a time, and may be performed three times, and the total time required may be from 45 minutes to 1 hour and 30 minutes.

The step of sterilization (S500) corresponds to a sterilization step, in which the microorganisms, etc. present in the decellarized material produced after the performance of the step of cell removal (S300) are killed. The step of sterilization (S500) is performed using a sterilization solution, and the sterilization solution may include peracetic acid that is effective in destroying the cell membrane of a microorganism. The sterilization solution may include phosphate buffered saline (PBS). In an embodiment, the sterilization solution may include the PBS and 1% peracetic acid. The step of sterilization (S500) may be performed by mixing the decellularized material and the sterilization solution and stirring appropriately using a stirrer. The step of sterilization (S500) may be performed at room temperature and may be performed for one hour or more of time.

The step of tertiary washing (S600) is performed to remove impurities and the sterilization solution after the step of sterilization (S500). In an embodiment, the step of tertiary washing (S600) may be performed at room temperature using distilled water, as in the step of primary washing (S200) and the step of secondary washing (S400). The step of tertiary washing (S600) may be performed for complete removal of the sterilization solution for 15 to 30 minutes at a time, in a manner similar to the step of primary washing (S200) and the step of secondary washing (S400), may be performed 3 times, and the total time required may be from 45 minutes to 1 hour and 30 minutes.

The process for producing a bioink raw material of the kidney may include a process of treating the decellularized material to a state suitable for use as a bioink material of the kidney as described above. The process for producing a bioink raw material may include a step of primary freeze-drying (S700), a step of tissue lysis (S800), a step of pH adjustment and dilution step (S900), and a step of secondary freeze-drying (S1000).

The step of primary freeze-drying (S700) is performed such that moisture is removed from the decellularized material in which sterilization is performed thereby capable of minimizing protein modification. When the decellularized material is dried, the step of tissue lysis (S800) to be described later can easily be performed.

The step of tissue lysis (S800) corresponds to a step for preparing the step of pH adjustment and dilution (S900) to be described later. The step of tissue lysis (S800) may be performed by lysing the tissue in a solution containing acetic acid. In an embodiment, acetic acid may be dissolved to a concentration of about 0.5 M, and the material concentration may be dissolved to a concentration of less than 0.5%.

The step of pH adjustment and dilution (S900) is performed such that proteins favorable for kidney treatment can be amalgamated by the addition of functional proteins and/or decomposition of unwanted proteins with the inclusion digestion enzymes at its appropriate pH for optimal enzymatic activity. For example, the step of pH adjustment and dilution (S900) may be performed such that decorin and biglycan, which are a type of glycoproteins contained only in the tubules and blood vessels of the kidney, among the lysed decellularized materials that have undergone the step of tissue lysis (S800) are decomposed. The step of pH adjustment and dilution (S900) can decompose decorin and biglycan, and in an embodiment, MMP-13 may be selected as the enzyme. In an embodiment, the step of pH adjustment and dilution (S900) may be performed by, for example, generating MMP-13 at a concentration of 2 μM or higher and stirring the lysed decellularized material together. In an embodiment, when the step of pH adjustment and dilution (S900) may be performed in about 5 hours, for example, when the time required for the entire decellularization process is 40 hours.

The step of secondary freeze-drying (S1000) is performed such that moisture is removed from the lysed material. The material that has undergone a decellularization process can be in a state suitable for future use as a bioink when the moisture contained in the material is removed. The freeze drying may be performed by loading the decellularized material, which is contained in a predetermined container, on a freeze dryer. In an embodiment, the freeze drying may be performed such that the decellularized material contained in the 50 mL tube is cooled and the tube is laid down to increase the reaction surface area. In an embodiment, the secondary freeze-drying may be performed at a pressure of less than 15 Pa and a temperature below −60° C., and may be performed for about 3 days to minimize the moisture content.

After the step of secondary freeze-drying (S1000) is performed, a step of secondary lysis with a bioink may be performed. The step of secondary lysis lyses the decellularized material by stirring it in acetic acid, and the concentration of the material is performed so as to lyse all of the decellularized materials that were produced and dried to a concentration of about 1%. In an embodiment, when the concentration of the material is about 1%, the step of secondary lysis may be performed for about 48 hours.

The decellularized material that has undergone the step of secondary lysis may be supplied into the body in various ways, for example, it may be directly injected into the body or may be mixed with a hydrogel and then injected into the body, or a specific water tank may be formed through 3D printing and used as an implant, etc.

FIGS. 3A, 3B, 3C, 3D, 3E and 3F shows images illustrating a decellularized material of kidney tissue according to an embodiment.

In FIGS. 3A, 3B, 3C, 3D, 3E and 3F, among the above-mentioned decellularization of kidney tissue, step of preparing the kidney tissue secured (FIG. 3A and FIG. 3B), step of primary washing (FIG. 3C), and step of cell removal (FIG. 3D), step of pF adjustment (FIG. 3E), and step of freeze-drying (FIG. 3F) are shown by photographing the decellularized material.

Figure 4:
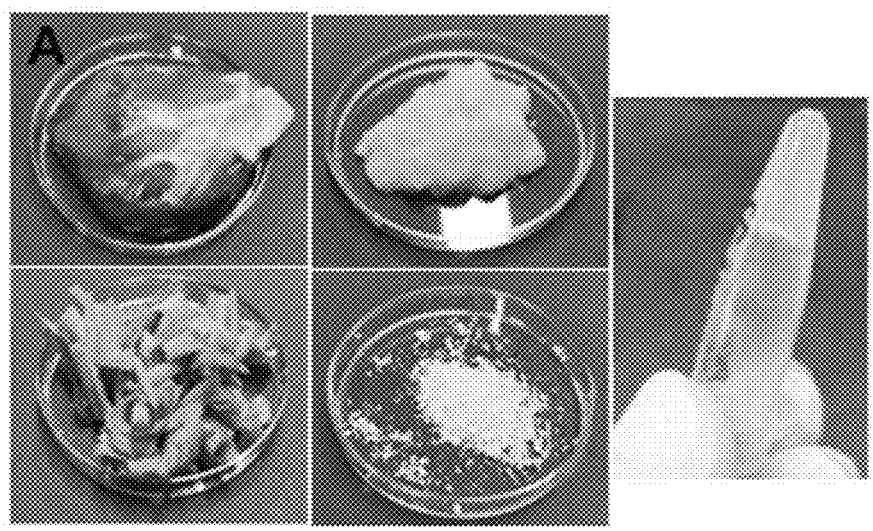
FIG. 4 shows images illustrating a bioink containing a decellularized material of kidney tissue according to an embodiment.

FIG. 4 shows images illustrating a bioink containing a decellularized material of kidney tissue according to an embodiment. As illustrated in FIG. 4, a bioink can be produced by lysing the above-mentioned decellularized material and stirring it with a hydrogel. The hydrogel may be constituted by containing at least one of gelatin and collagen. Hydrogels can be changed to liquid and gel states at specific temperatures or at specific pH conditions. In the case of producing long-term chips by printing, the hydrogel is provided with an appropriate property for the decellularized material to be printed during the manufacturing process, and it becomes an unnecessary component after the manufacture. Therefore, since its removal is desirable, after printing is completed, an appropriate temperature change is provided to change the phase to a liquid, and then only the hydrogel can be removed from a 3D structure. The hydrogel can be liquefied below a predetermined temperature and can be solidified above a predetermined temperature.

Hereinafter, effects and confirmation of the decellularized material according to the present invention will be described with reference to FIGS. 5 to 12B.

Figure 5:
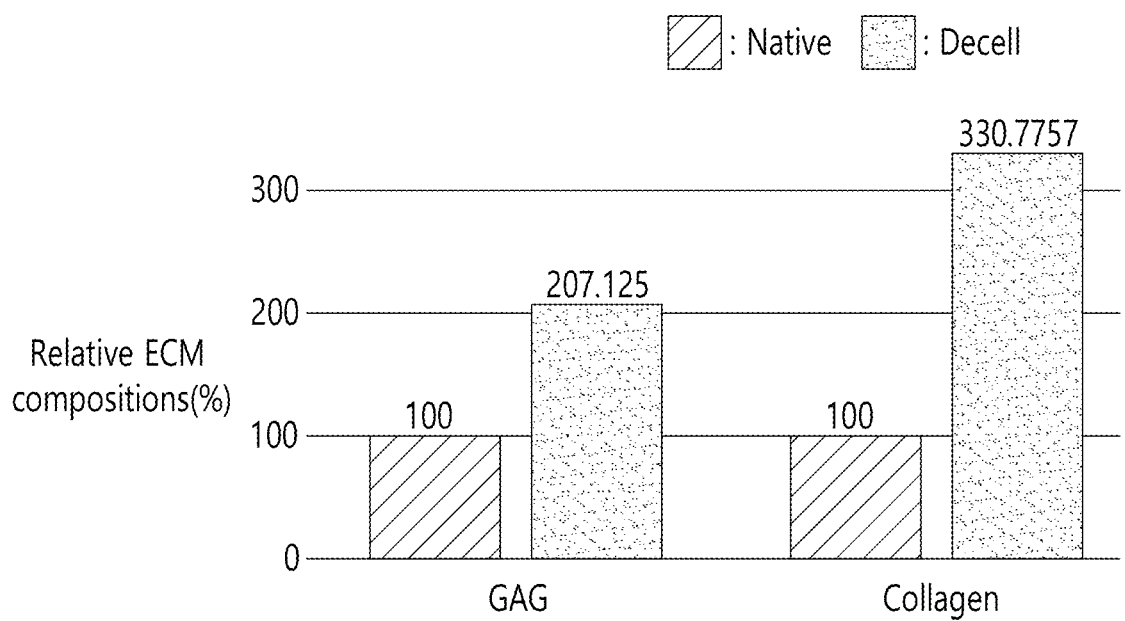
FIG. 5 is a graph illustrating quantitative evaluation of extracellular matrix content of a decellularized material of kidney tissue.

FIG. 5 is a graph illustrating quantitative evaluation of extracellular matrix content of a decellularized material of kidney tissue.

As illustrated in FIG. 5, it can be confirmed that the decellularized material contains about 2 times of a GAG content and about 3 times of a collagen content compared to natural cells. As used herein, "Relative ECM composition %" refers to the relative percentage of ECM in tissue, that is, the percentage of extracellular matrix components; and glycosaminoglycans (GAG) refers to a polysaccharide which is a major extracellular matrix component, and collagen is a light protein, also called "collagen", which refers to a main component of connective tissue in tissues.

Figure 6:
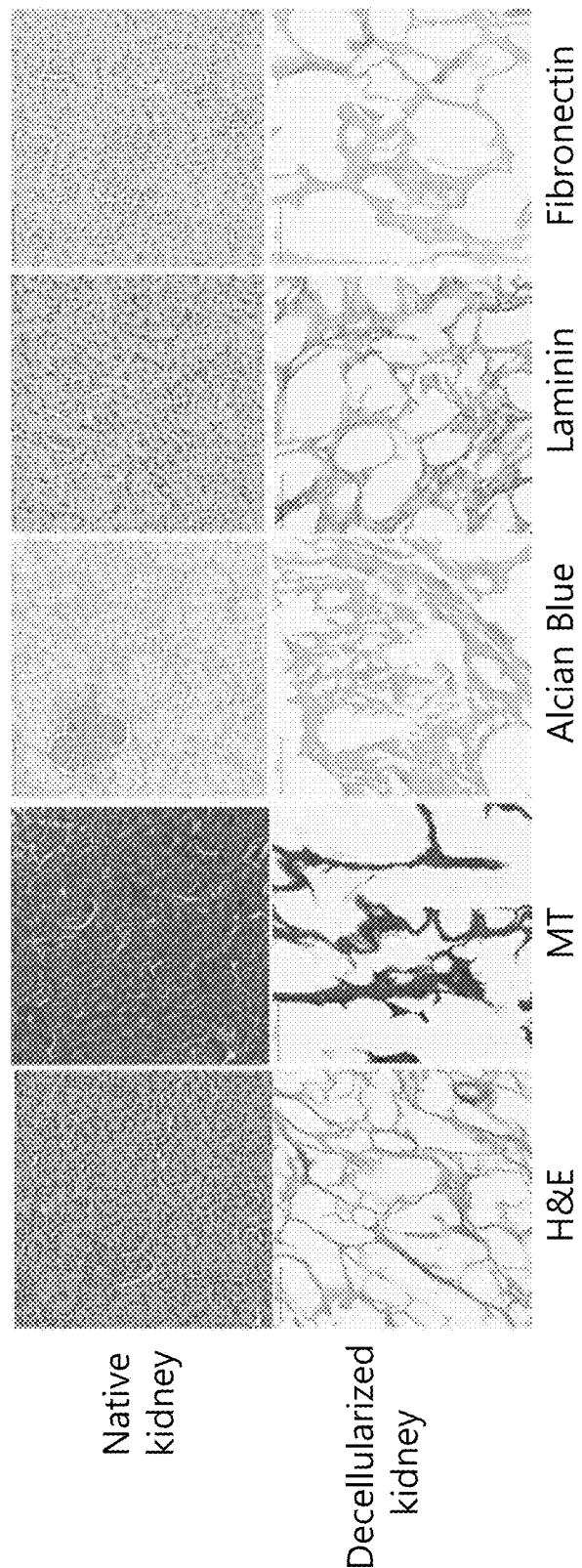
FIG. 6 shows images illustrating an active ingredient specialized in the treatment of kidney tissue of a decellularized tissue.

FIG. 6 shows images illustrating an active ingredient specialized in the treatment of kidney tissue of a decellularized tissue.

As illustrated in FIG. 6, Hematoxylin & Eosin (H&E), Masson's Trichrome (MT), Alcian Blue, laminin, fibronectin are shown as examples of active ingredients specialized in the treatment of kidney tissue.

The amount of cells remaining in the decellularized material produced through the decellularization method according to the present invention was confirmed through H&E staining; and that the remaining of main components of the extracellular matrix of kidney tissue by MT, Alcian Blue, staining, etc. In addition, the remaining of active ingredients effective in treating kidneys (e.g., laminin, fibronectin, etc.) can be confirmed through immunohistochemistry.

Figure 7A:
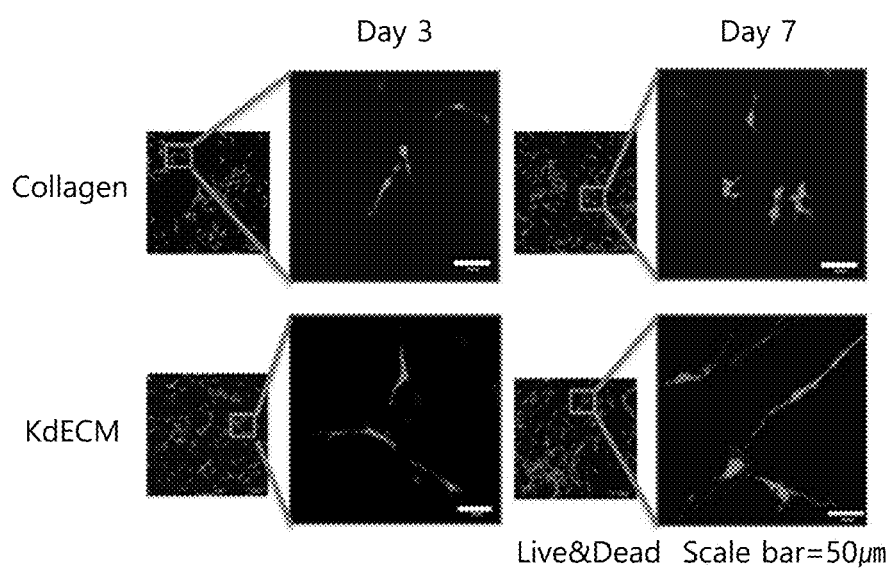
FIGS. 7A and 7B shows images illustrating the rate of cell viability of kidney cells in a decellularized material.
Figure 7B:
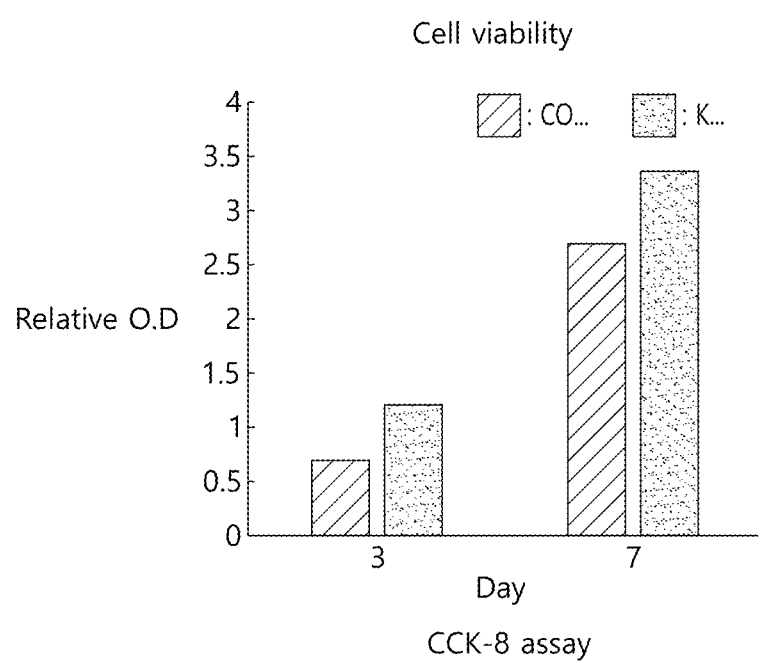

FIGS. 7A and 7B shows images illustrating the rate of cell viability of kidney cells in a decellularized material. As illustrated, it is possible to compare the case where kidney-derived cells are cultured in collagen and the case where kidney-derived cells are cultured in a decellularized material of kidney tissue. The images illustrated are those of 3 and 7 days after the start of cultivation, and upon comparison of the images, it was confirmed that the cell viability rate of the kidney-derived cells cultured in a decellularized material of kidney tissue was significantly higher.

Figure 8:
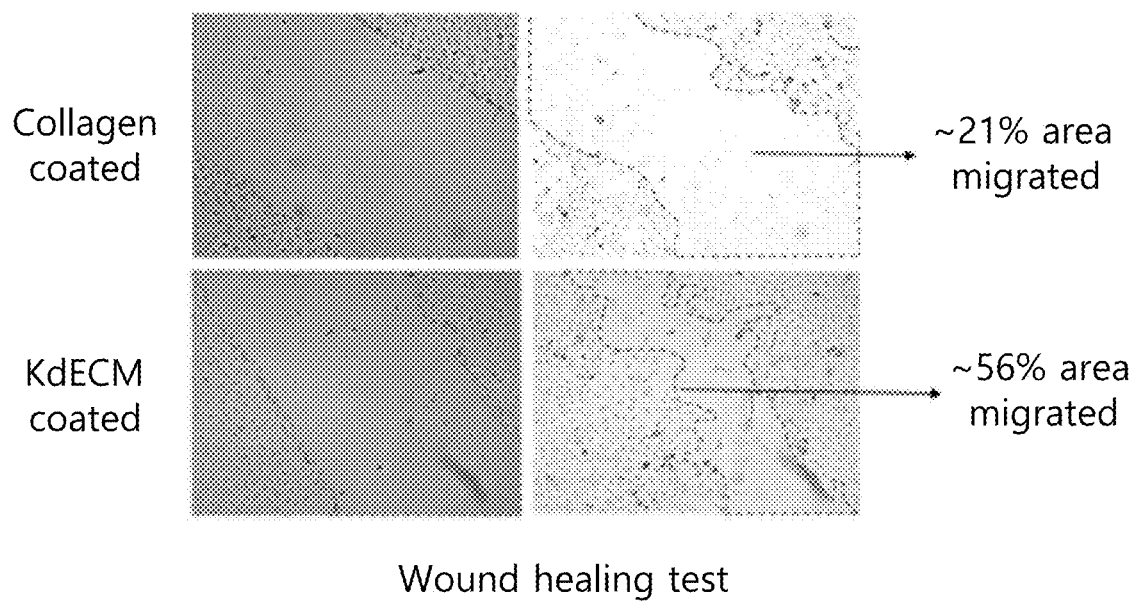
FIG. 8 shows images illustrating the regeneration effect of kidney tissue when printed using a decellularized material.

FIG. 8 shows images illustrating the regeneration effect of kidney tissue when printed using a decellularized material. In this figure, when there is damage or wound of kidney tissue, it is possible to confirm the effect of regeneration when collagen or a decellularized material is applied to the damaged site. With respect to the above-described two cases, it was confirmed that the regeneration effect was more than doubled when the decellularized material of kidney tissue was applied under the same conditions.

Figure 9:
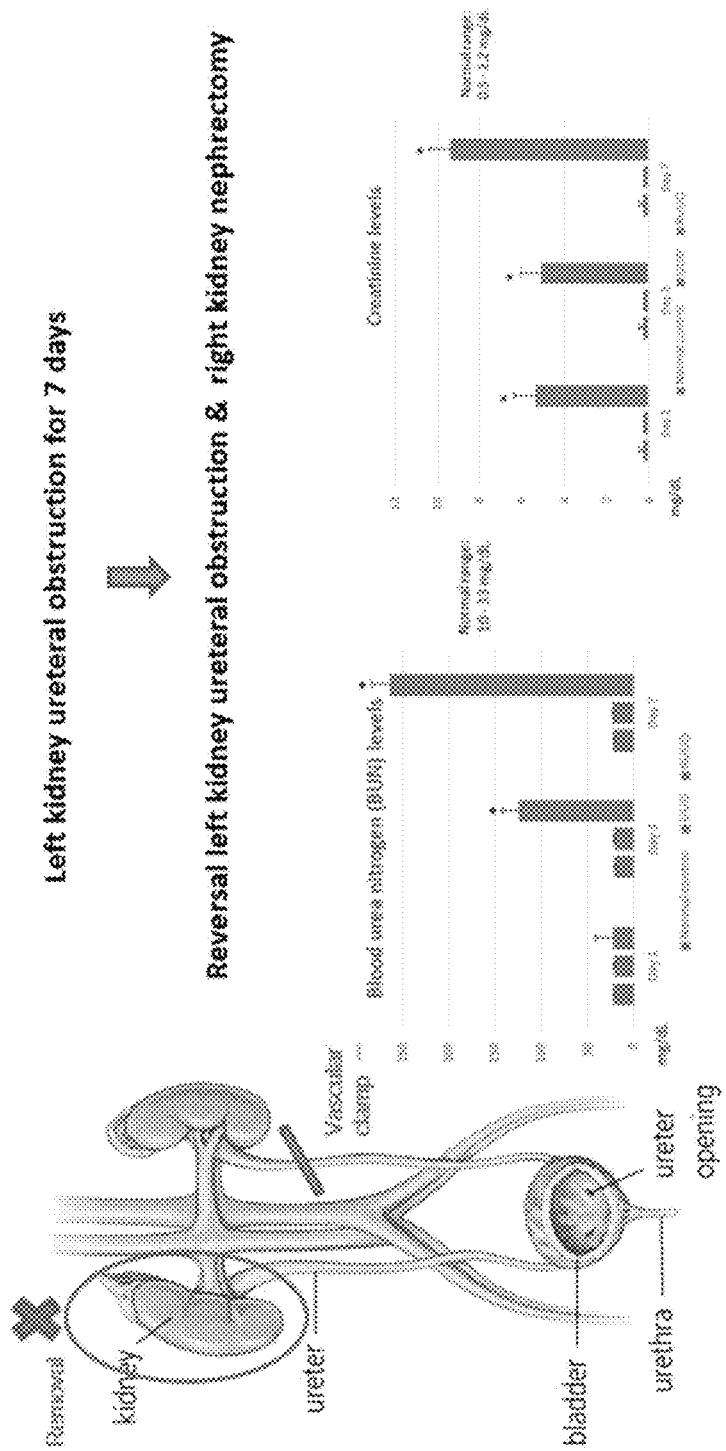
FIG. 9 shows drawings illustrating an animal experiment process for a decellularized material.
Figure 10:
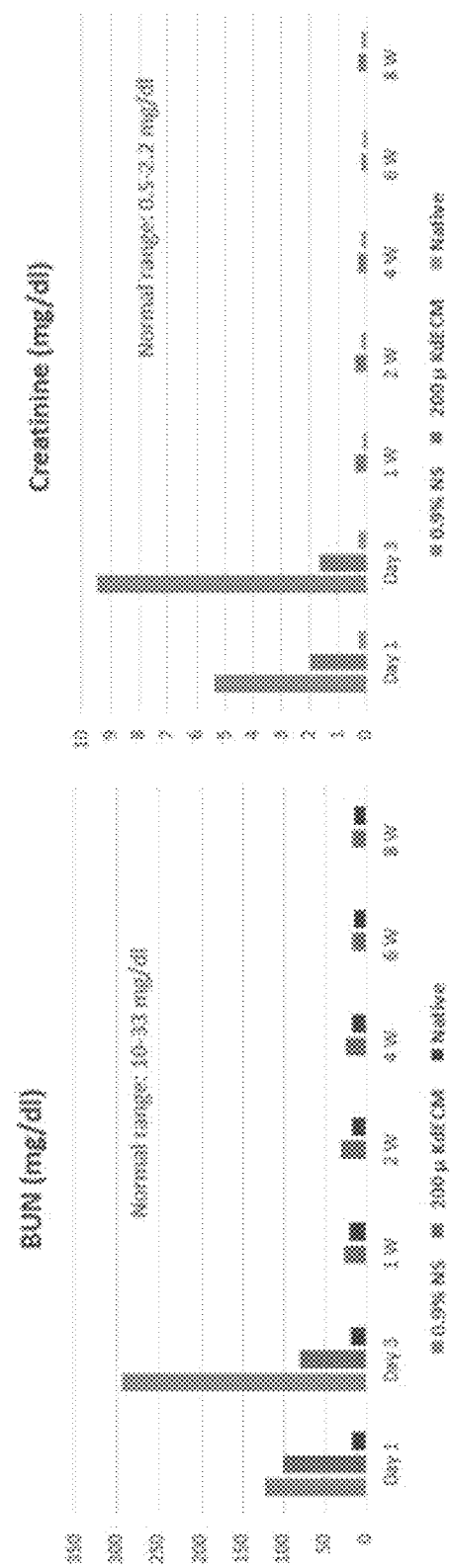
FIG. 10 shows graphs illustrating the results of animal experiments for a decellularized material.

FIG. 9 shows drawings illustrating an animal experiment process for a decellularized material; and FIG. 10 shows graphs illustrating the results of animal experiments for a decellularized material.

As illustrated, first, the left kidney was artificially damaged by temporarily obstructing the left kidney ureteral of a mouse. In this experiment, when the left ureter was closed for 7 days, the levels of blood urea nitrogen increased rapidly, and creatinine levels also increased rapidly, thus confirming the occurrence of damage to the left kidney. Thereafter, the right kidney was excised (kidney nephrectomy) and the closed left ureter was opened, and thereby created a state where only the damaged left kidney could function.

Subsequently, according to the present invention, the decellularized material derived from kidney tissue was administered to the left kidney and the progress was examined for about 8 weeks, and as a result, it was confirmed that the levels of blood urea nitrogen and creatinine were recovered to normal values within a week. As an example of a method for administering the decellularized material to the kidney, the administration may be performed by injecting the decellularized material into a lesion site using a syringe. In this experiment, the decellularized material in an amount of 200 μL to 5 mL was injected into the renal medulla region opposite the renal arteriovenous region where the lesion occurred. Meanwhile, when injecting the decellularized material into the kidney, the abdomen of the subject for experiment may be opened or the decellularized material may be injected into the kidney using an abdominal ultrasound guide. However, these are only embodiments, and the injection can be made by approaching the lesion site of the kidney in various ways.

Figure 11:
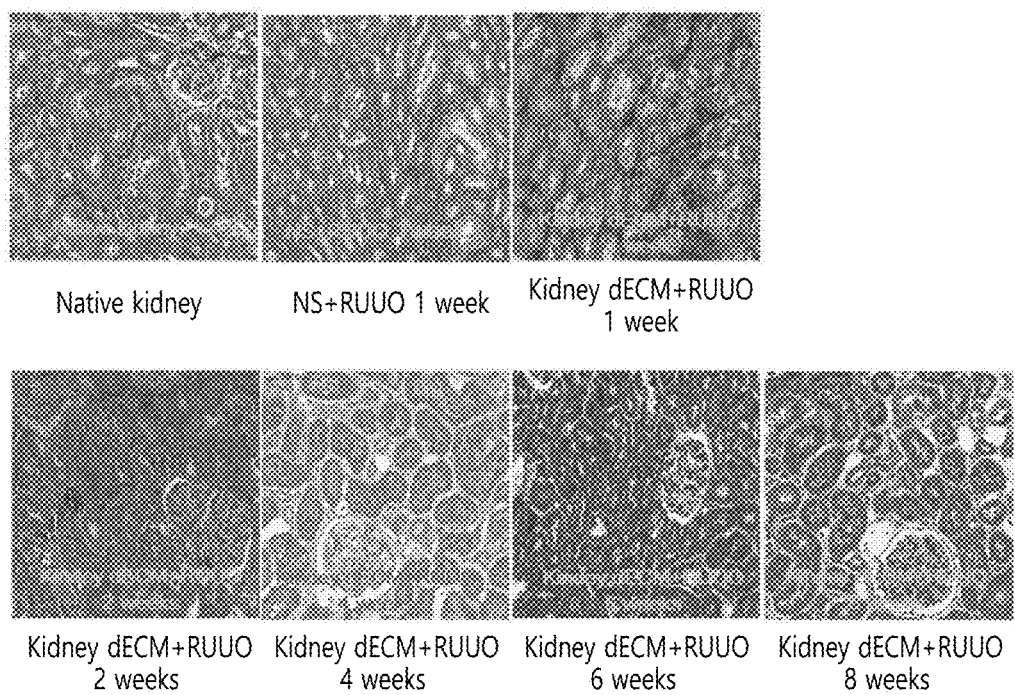
FIG. 11 shows images illustrating the effects of a decellularized material according to an embodiment on the anti-fibrosis and regeneration capacity of kidney tissue.
Figure 12A:
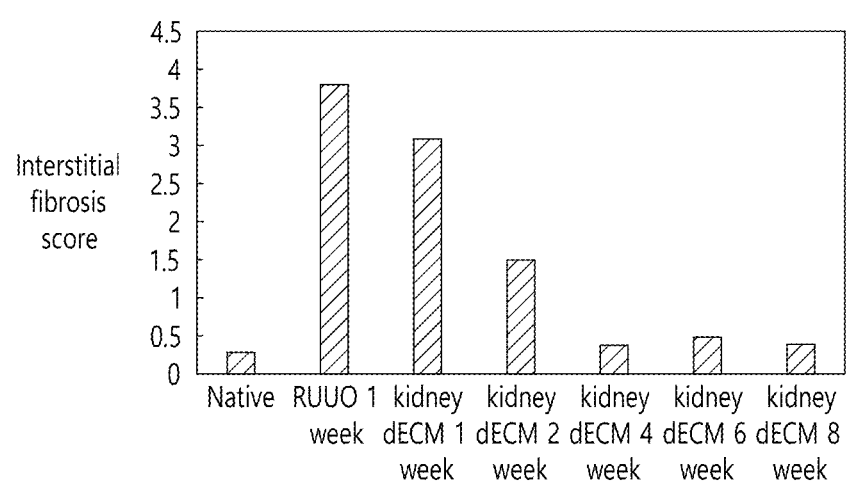
FIGS. 12A and 12B shows graphs illustrating the antifibrosis levels in kidney tissue from a patient with chronic renal failure disease.
Figure 12B:
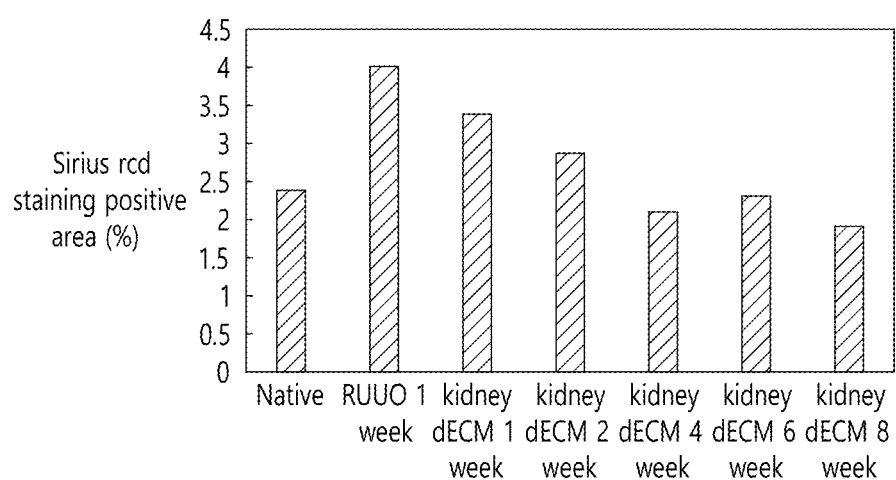

FIG. 11 shows images illustrating the effects of a decellularized material according to an embodiment on the antifibrosis and regeneration capacity of kidney tissue; and FIG. 12A and FIG. 12B shows images illustrating the values of the antifibrosis and regeneration capacity of kidney tissue in a decellularized material.

Referring to FIG. 11, images are illustrated 1, 2, 4, 6, and 8 weeks after the injection of a decellularized material derived from normal kidney tissue, kidney fibrosis-induced tissue, and kidney tissue, and it can be confirmed that significant portions of the tissue that had undergone fibrosis after four weeks were recovered.

Referring to FIGS. 12A and 12B, the fibrosis level may be an example of an evaluation factor for the treatment of a lesion site of the kidney. The levels of kidney fibrosis can be calculated by direct histopathological examination of kidney tissue in the lesion. In an embodiment of the histopathological examination for calculating the levels of kidney fibrosis, the kidney tissue in the lesion is collected and then subjected to Masson's trichrome staining and sirius red staining (methods to identify the degree of interstitial fibrosis and interstitial collagen deposition of kidney tissue), and the degree of fibrosis can be expressed numerically by dividing them into grades as shown in Table 1 below, according to the degree of staining in the cross-sectional area of kidney tissue.

TABLE 1

| Range of staining (staining positive) | Grade |
| --- | --- |
| No staining | 0 |
| 25% Staining | 1 |
| 25 to 50% Staining | 2 |
| 50 to 75% Staining | 3 |
| 75 to 100% staining | 4 |

Meanwhile, "native" shown in FIGS. 12A and 12B refers to normal kidney tissue, and "RUUO", which is a reversible unilateral ureteral obstruction, refers to a state in which kidney fibrosis has occurred by a kidney fibrosis-inducing method.

Referring to FIG. 12A, with respect to the interstitial fibrosis score, the recovery progressed actively until 4 weeks after the injection of the decellularized material, confirming that the fibrosis score was rapidly reduced, and it was confirmed that the fibrosis score was maintained stably after 4 weeks.

Additionally, referring to FIG. 12B, it was confirmed that the sirius red staining area increased to the maximum value since RUUO and then the value gradually decreased after the injection of the decellularized material derived from kidney tissue, and after 4 weeks, the value was shown to be similar to that of normal kidney tissue.

As described above, the method for decellularization of kidney tissue, which is an embodiment according to the present invention, can produce a decellularized material in a state where a protein effective in the kidney is decomposed, and the produced decellularized material is constituted by mimicking the extracellular matrix composition constituting the basal membrane of the kidney's glomerulus, and thus kidney treatment can be maximized when the decellularized material is used.

Additionally, when a bioink used for 3D printing is produced using the decellularized material produced according to the present invention, it is possible to print the decellularized material in a structure with a desired shape while securing the above-mentioned effect of kidney treatment.

The method for decellularization of kidney tissue according to the present invention, the decellularized material produced through the method, and a bioink comprising the decellularized material have the effect of maximizing the effect of kidney treatment by maximizing the content of components specialized for kidney treatment such as the collecting duct and renal tubule of the kidney.

What is claimed is:

1. A method for decellularization of kidney tissue, comprising:
    a step of preparing kidney tissue, in which the kidney tissue extracted from a mammal to be a subject of decellularization is cut into pieces having a thickness of about 2 mm or less;
    a step of removing cells, in which the cells of the kidney tissue are converted to a decellularized material using a decellularization solution that comprises a surfactant and a hypertonic solution;
    a step of sterilization, in which the decellularized material and a sterilization solution are stirred such that microorganisms present in the decellularized material are killed; and
    a step of pH adjustment and dilution, in which an enzymatic reaction is performed such that glycoproteins in the decellularized material are decomposed,
    wherein the surfactant is 2-[4-(2,4,4-trimethylpentan-2-yl)phenoxy]ethanol,
    wherein the step of pH adjustment and dilution is performed using MMP-13 at a concentration of 2 μM to 1 M,
    wherein the sterilization solution is a solution comprising peracetic acid, and
    wherein the hypertonic solution is a NaCl solution of 0.3M to 1.0M.

2. The method of claim 1, wherein the glycoproteins decomposed in the step of pH adjustment and dilution are at least one of decorin and glycan.

3. The method of claim 2, wherein the step of pH adjustment and dilution is performed for 3 to 5 hours.

4. The method of claim 2, wherein after the step of preparing kidney tissue, the step of removing cells, and the step of sterilization, further comprising a step of washing, in which the remaining solution and impurities are washed.

5. The method of claim 4, wherein the step of washing is performed by stirring the kidney tissue or decellularized material along with a washing solution.

6. The method of claim 5, wherein after the step of removing cells, a step of sterilization is performed, in which a sterilization solution and the decellularized material are stirred such that the microorganisms present in the decellularized material are killed.

7. The method of claim 6, wherein the sterilization solution further comprises phosphate buffered saline (PBS).

8. The method of claim 2, wherein before and after performing the step of pH adjustment and dilution, further comprising a step of freeze drying that is performed at least once.

* * * * *